US009936926B2

(12) United States Patent
Eronen

(10) Patent No.: US 9,936,926 B2
(45) Date of Patent: Apr. 10, 2018

(54) SYSTEM AND METHOD OF SMALL FIELD OF VIEW X-RAY IMAGING

(71) Applicant: PaloDEx Group Oy, Tuusula (FI)

(72) Inventor: Esa Kalevi Eronen, Littoinen (FI)

(73) Assignee: PaloDEx Group Oy, Tuusula (FI)

( * ) Notice: Subject to any disclaimer, the term of this patent is extended or adjusted under 35 U.S.C. 154(b) by 493 days.

(21) Appl. No.: 14/611,865

(22) Filed: Feb. 2, 2015

(65) Prior Publication Data
US 2016/0220201 A1 Aug. 4, 2016

(51) Int. Cl.
A61B 6/06 (2006.01)
A61B 6/03 (2006.01)
(Continued)

(52) U.S. Cl.
CPC .............. *A61B 6/4035* (2013.01); *A61B 6/06* (2013.01); *A61B 6/035* (2013.01); *A61B 6/14* (2013.01); *A61B 6/4085* (2013.01); *A61B 6/5211* (2013.01)

(58) Field of Classification Search
CPC .. A61B 6/00; A61B 6/03; A61B 6/032; A61B 6/035; A61B 6/06; A61B 6/40; A61B 6/4035; A61B 6/4042; A61B 6/4064; A61B 6/4085; A61B 6/44; A61B 2560/00; A61B 2560/06; G21K 1/00; G21K 1/02; G21K 1/04; G21K 1/043; G21K 1/046; G21K 1/10; G21K 2201/00; H01J 3/00; H01J 3/08; H01J 3/12; H01J 29/46; H01J 29/52; H01J 29/56; H01J 29/563; H01J 29/89; H01J 29/898; H01J 35/00; H01J 2237/00; H01J 2237/04; H01J 2237/045; H01J 2237/0455; H01J 2237/06; H01J 2237/065; H01J 2237/0653; H05G 1/00; H05G 1/02; G01N 2223/10; G01N 2223/101; G01N 2223/1016; G01N 2223/20;
(Continued)

(56) References Cited

U.S. PATENT DOCUMENTS 5,278,887 A * 1/1994 Chiu ..................... G21K 1/10
378/156
5,528,644 A 6/1996 Ogawa et al.
(Continued)

OTHER PUBLICATIONS

Extended European Search Report in corresponding EP Application No. 16153736.0, dated Jun. 24, 2016.

*Primary Examiner* — Anastasia Midkiff
(74) *Attorney, Agent, or Firm* — Andrus Intellectual Property Law, LLP

(57) ABSTRACT

A system and method of X-ray imaging includes an X-ray emitter that projects X-rays. An X-ray receiver receives X-rays from the X-ray emitter to produce a plurality of projection images. A filter with at least one filter leaf absorbs at least a portion of the X-rays from the X-ray emitter to define a limited field of view within a full field of view, wherein the X-rays are attenuated in at least one attenuated portion of the full field of view. A processor reconstructs a three dimensional image based upon the projection images of the full field of view. The limited field view is located within the reconstructed three dimensional image. At least one corrective parameter is determined from the reconstructed three dimensional image. A three dimensional image is reconstructed based upon the limited field of view and the at least one corrective parameter.

17 Claims, 3 Drawing Sheets

(51) Int. Cl.
*A61B 6/00* (2006.01)
*A61B 6/14* (2006.01)

(58) Field of Classification Search
CPC ......... G01N 2223/206; G01N 2223/30; G01N 2223/313; G01N 2223/316; G01N 2223/32; G01N 2223/40; G01N 2223/423; A61N 2005/1092; A61N 2005/1095; H04N 1/0289
See application file for complete search history.

(56) References Cited

U.S. PATENT DOCUMENTS

| | | | |
|---|---|---|---|
| 6,501,828 B1* | 12/2002 | Popescu | A61B 6/06 378/145 |
| 7,076,029 B2* | 7/2006 | Toth | A61B 6/032 378/158 |
| 7,082,189 B2* | 7/2006 | Yahata | A61B 6/06 378/156 |
| 7,756,315 B2 | 7/2010 | Hsieh et al. | |
| 8,107,708 B2 | 1/2012 | Hoppe et al. | |
| 8,155,415 B2 | 4/2012 | Faul et al. | |
| 8,861,679 B2 | 10/2014 | Suuronen et al. | |
| 2004/0066885 A1 | 4/2004 | Ogawa | |
| 2011/0058722 A1 | 3/2011 | Hu et al. | |
| 2011/0261926 A1* | 10/2011 | Hangartner | A61B 6/032 378/19 |
| 2012/0057674 A1* | 3/2012 | Zhang | A61B 5/7285 378/62 |
| 2013/0182820 A1 | 7/2013 | Proksa | |
| 2013/0294570 A1 | 11/2013 | Hansis | |
| 2013/0308747 A1 | 11/2013 | Abraham et al. | |
| 2014/0112441 A1* | 4/2014 | Becker | A61B 6/032 378/62 |
| 2014/0328453 A1* | 11/2014 | Hsieh | A61B 6/035 378/16 |

* cited by examiner

SYSTEM AND METHOD OF SMALL FIELD OF VIEW X-RAY IMAGING

FIELD

The present disclosure relates to X-ray imaging systems and methods,.

BACKGROUND

U.S. Pat. No. 8,155,415 discloses an apparatus and method for expanding the field of view of a truncated computed tomography (CT) scan. An iterative calculation is performed on the original CT image to produce an estimate of the image. The calculated estimate of the reconstructed image includes the original image center and an estimate of the truncated portion outside the image center. The calculation uses an image mask with the image center as one boundary.

U.S. Pat. No, 8,107,708 discloses a method for correcting truncation artifacts in a reconstruction method for computed tomography recordings. The projection images are recorded by an X-ray image detector being extended by determining the attenuation of the radiation outside the projection image for pixels. Non-horizontal filter lines are extended by transaxial and axial artificial extension of the X-ray image detector for the purposes of truncation correction.

U.S. Pat. No. 7,756,315 discloses a method for expanding a field-of-view of a volumetric computed tomography scan. The method includes identifying truncated views having projection truncation and non-truncated views without projection truncation based on an average value of one or more edge channels. An estimated missing projection is calculated for each of the truncated views based on at least one neighboring non-truncated view. A projection profile is calculated for each of the truncated views based on the estimated missing projection, and the projection profile provides at least one of attenuation data and projection data for an area outside a field-of-view.

U.S. Pat. No. 5,278,887 discloses an apparatus and method for reducing the dosage of X-rays during a fluoroscopic procedure. A filter member is used to selectively attenuate the X-ray radiation striking a patient's body. The filter member allows unattenuated X-rays to image an area of interest selected by a physician, thus producing a high intensity, low noise image. Areas surrounding the area of interest are imaged with attenuated radiation producing; a less intense, more noisy image.

U.S. patent application Ser. No. 12/990,285 discloses a method of using non-attenuation corrected PET emission images to compensate for incomplete anatomic images. A segmented contour of a non-attenuation-corrected (NAC) PET image is used to identify a contour of the truncated region. An appropriate tissue type is used to fill in truncated regions of a truncated CT or MR image or the attenuation map. The corrected attenuation map is then used to generate an attenuation-corrected PET image of the patient or a region of interest.

U.S. patent application Ser. No. 13/113,714, which is hereby incorporated by reference in its entirety, discloses X-ray imaging systems and methods that utilize an imaging apparatus that includes an emitter emitting X-rays through an object and a receiver receiving the X-rays. A control circuit controls the emitter and processes the X-rays received by the receiver to generate X-ray images of the object. The control circuit controls a display to display an initial view of the object. The display of the initial view of the object is modifiable by a user. The imaging apparatus is controlled to generate an X-ray position image of the object based upon the user modification of the display of the initial view. The display is controlled to display a positioning image. The display of the positioning image is modifiable by a user and the imaging apparatus is controlled to generate an X-ray image of the object based upon the user modification of the display of the positioning image.

BRIEF DISCLOSURE

An exemplary embodiment of an X-ray imaging system includes an X-ray emitter that projects X-rays through an object which at least partially absorbs the X-rays. An X-ray receiver is configured to receive unabsorbed X-rays from the X-ray emitter and produces projection images of the object from the received unabsorbed. X-rays. A filter is disposed between the X-ray emitter and the X-ray receiver. The filter includes at least one filter leaf that absorbs at least a portion of the X-rays from the X-ray emitter. The at least one filter leaf is adjustable to adjust an amount of X-ray intensity applied to the object in at least a full field of view and a limited field of view. A processor is connected to the X-ray receiver. The processor executes computer readable code stored upon a computer readable medium and upon execution of the computer readable code processes the projection images from the X-ray receiver. The processor reconstructs a three dimensional image based upon projection images of the full field of view. The processor locates the limited field of view within the reconstructed three dimensional image based upon the full field of view. The processor identifies at least one corrective parameter from the reconstructed three dimensional image. The processor reconstructs a three dimensional image based upon the limited field of view with the at least one corrective parameter.

A method of X-ray imaging includes projecting X-rays from an X-ray emitter. The X-rays are filtered with at least one filter leaf that absorbs at least a portion of the projected X-rays to define a limited field of view within a full field of view. The X-ray intensity is attenuated in at least one attenuated portion of the full field of view. The X-rays are received at an X-ray receiver to acquire a plurality of projection images from the limited field of view and the full field of view. A processor reconstructs a three dimensional image based upon the projected images from the full field of view. The processor locates the limited field of view within the reconstructed three dimensional image. The processor defines at least one corrective parameter from the located limited field of view. The processor reconstructs a three dimensional image based upon the projected images from the limited field of view and the at least one corrective parameter.

DETAILED DISCLOSURE

In the present description, certain terms have been used for brevity, clearness and understanding. No unnecessary limitations are to be implied therefrom beyond the requirement of the prior art because such terms are used for descriptive purposes only and are intended to be broadly construed. The different systems and methods described herein may be used alone or in combination with other systems and methods. Various equivalents, alternatives and modifications are possible within the scope of the appended claims. Each limitation in the appended claims is intended to invoke interpretation under 35 U.S.C. § 112(f), only if the terms "means for" or "step for" are explicitly recited in the respective limitation.

Figure 1:
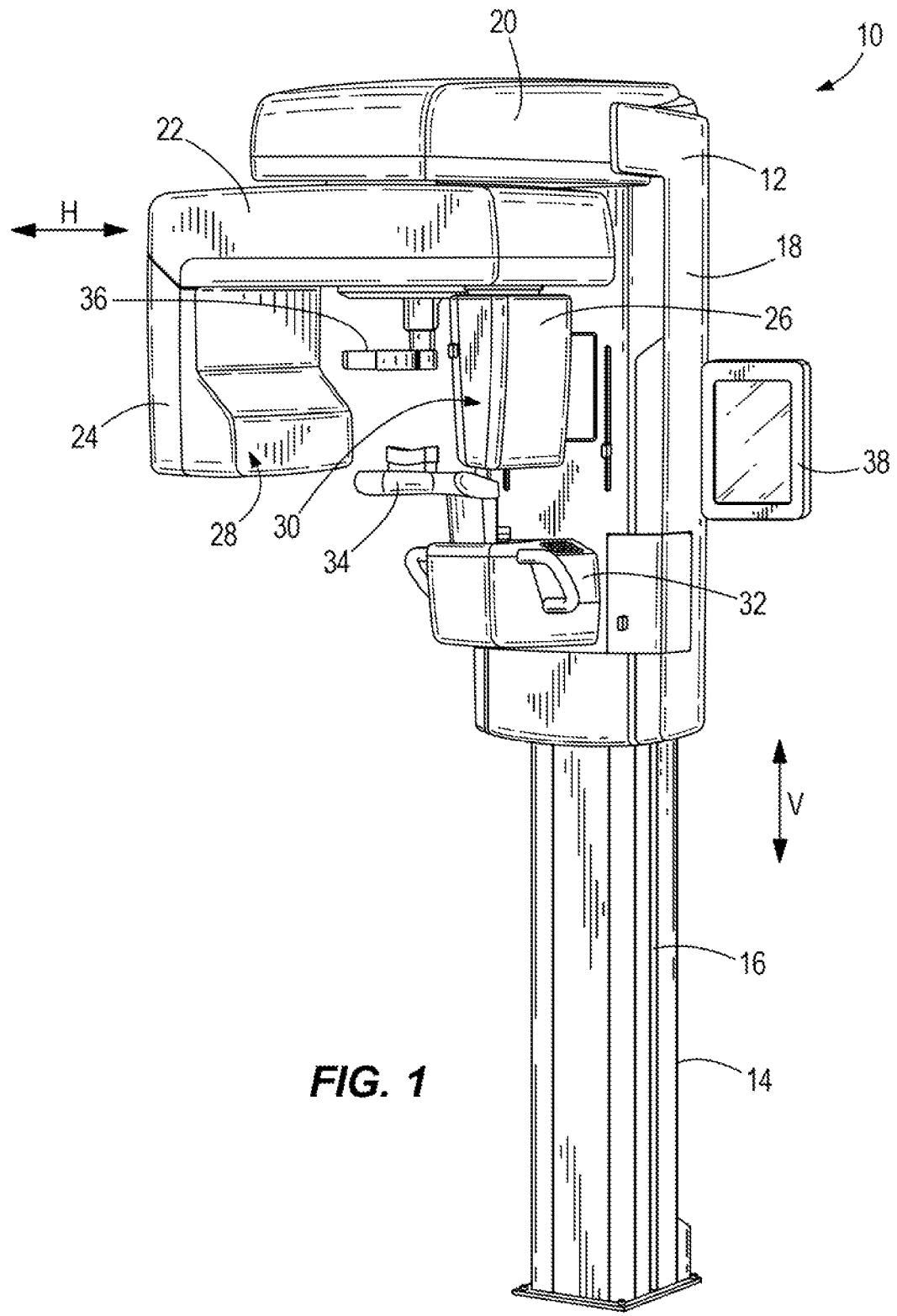
FIG. 1 is a perspective view of an exemplary X-ray imaging apparatus.

FIG. 1 depicts an exemplary X-ray imaging apparatus for acquiring X-ray images of an object, exemplarily a dental or medical patient. In the particular example shown, the imaging apparatus 10 is configured for 3-D imaging of the dentomaxillofacial complex of the human skull; however, other configurations of apparatuses for imaging of other portions of a patient's anatomy can instead be employed with the concepts of the present disclosure. The X-ray imaging apparatus 10 can optionally be configured to conduct different types of imaging procedures, including, but not limited to panoramic imaging (standard, pediatric, orthozone, wide arch, orthogonal and/or the like), cephalometric imaging (cephalo pediatric lateral projection, cephalo lateral projection, cephalo postero-anterior, and/or the like), and/or 3-D imaging. FIG. 1 depicts just one example of an X-ray imaging apparatus for use with the concepts in the present disclosure. Other examples of X-ray imaging apparatus can be instead be employed, including, but not limited to computed tomography (CT) and fluoroscopic imaging. Techniques and apparatus disclosed herein may also be used in connection with other forms of medical imaging and medical imaging modalities, and it is to be recognized that dental imaging is only an exemplary application.

The imaging apparatus 10 includes a housing 12 that is moveably supported on a support column 14. The housing 12 can be moved up and down in the vertical direction V via a conventional guide motor (not shown) that is configured to move the housing 12 vertically up and down along a track 16 extending along the support column 14. The housing 12 includes a generally vertically extending guide section 18 disposed on the support column 14 and a generally horizontally extending, support section 20 extending generally horizontally from the guide section 18. The support section 20 supports a rotating section 22, which is rotatable in a horizontal plane H with respect to the stationary support section 20. The support section 20 and/or rotating section 22 may contain a conventional (wide motor (not shown) configured to rotate the rotating section 22. In an alternative embodiment, the imaging apparatus 10 can be mounted to a support structure (not depicted) exemplarily a wall instead of, or in addition to, being supported by the column 14.

An X-ray emitter housing 24 and an X-ray receiver housing 26 are positioned on opposite ends of rotating section 22 and extend generally vertically downward from the rotating section 22. The emitter housing 24 contains an X-ray emitter generally located at 28, although not depicted, and supported in the emitter housing 24. The X-ray emitter is positioned to emit X-rays from the X-ray emitter through the object being imaged (e.g. the patient) to an X-ray receiver generally located at 30, although not depicted, supported in the X-ray receiver housing 26. A patient positioning housing 32 extends from the guide section 18 and includes a chin support 34 for positioning the head of the patient (not depicted) between the opposed X-ray emitter 28 and the X-ray receiver 30. A head support 36 extends from the horizontal support section 20 through the rotating section 22. The chin support 34 and the head support 36 may be optional, and positioning of the patient may be carried out in alternative manners. Embodiments of the imaging apparatus 10, further include a graphical display 38, for presentation of images as disclosed herein. In additional embodiments, the graphical display 38 may be a touch-sensitive graphical display that further operates as an input device to receive user input or control commands for the imaging apparatus 10.

Figure 2:
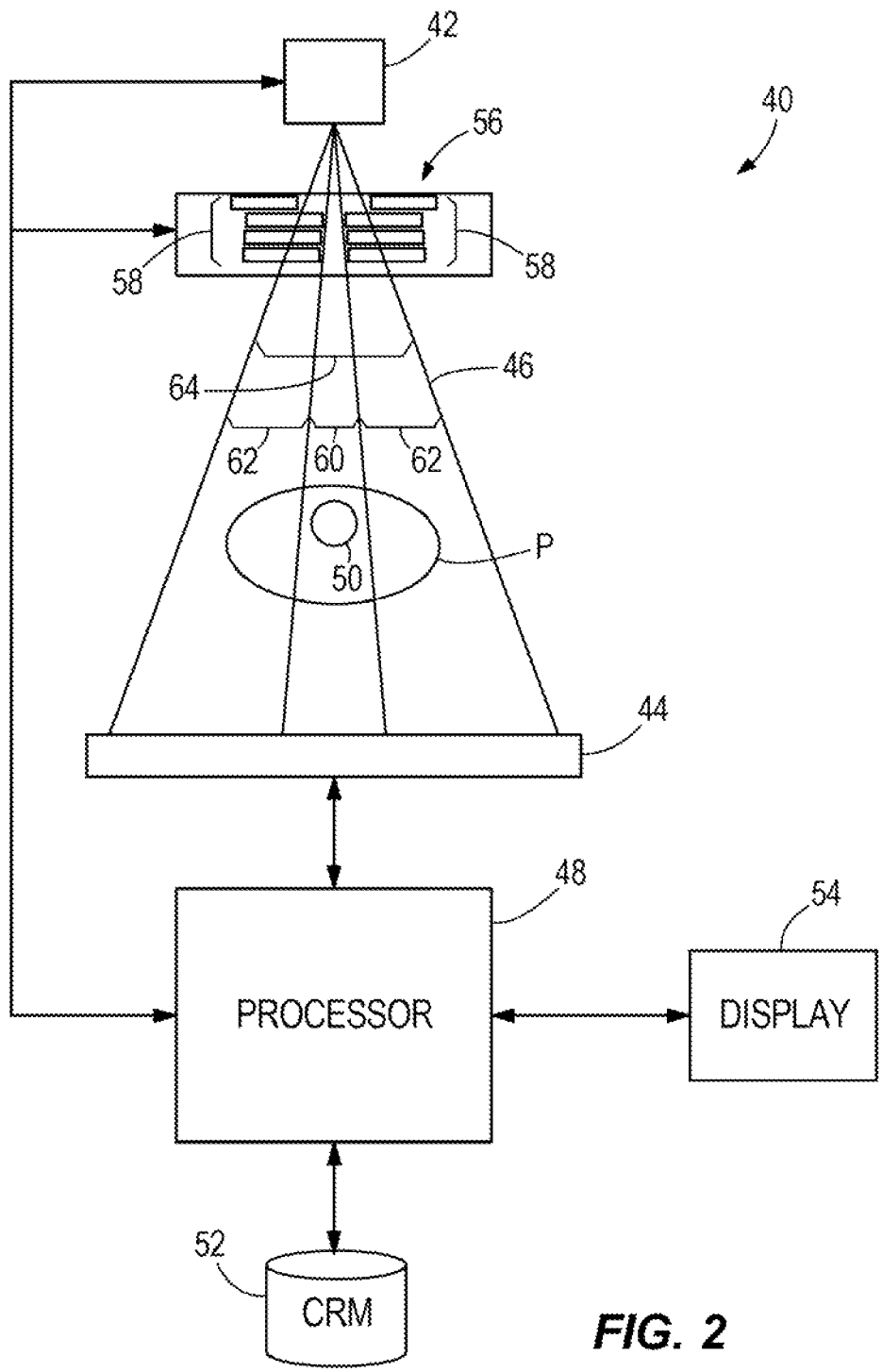
FIG. 2 is a schematic representation of an exemplary embodiment of an X-ray imaging system.

FIG. 2 is a schematic representation of an exemplary embodiment of an X-ray imaging system 40. As briefly described above, the X-ray imaging system 40 includes an X-ray emitter 42 and an X-ray receiver 44. The X-ray receiver 44 is spaced apart from the X-ray emitter 42 to accommodate an object, exemplarily a patient's head P, between the X-ray emitter 42 and the X-ray receiver 44. A beam 46 of X-rays is projected from the X-ray emitter 42 to the X-ray receiver 44 passing through the object P disposed there between. In a non-limiting embodiment, the beam 46 is a cone beam, although it would be recognized that alternative embodiments may use other beam shapes, including, but not limited to fan beam or line beams as may be recognized by one of ordinary skill in the art.

In operation, the X-ray emitter 42 projects the beam 46 in the direction of X-ray receiver 44. The X-rays pass through the patient's head P and the anatomical structures of the patient's head P absorb varying amounts of the X-rays. After passing through the patient P, the attenuated X-rays are absorbed at the X-ray receiver 44 that converts the intensity pattern of the received X-rays into a digitized output representative of the unabsorbed X-rays at the X-ray receiver 44. The X-ray receiver 44 provides this output to a processor 48. The collection of digitized output from the X-ray receiver 44 corresponding to a single emission of a beam of X-rays from the X-ray emitter 42 may be referred to as a projection image of the object P, exemplarily the patient's head. As used herein, projection images refer to a two dimensional array or matrix of data in which each matrix elements correlate to detected X-ray flux in a corresponding pixel. It is to be understood that, in embodiments, using storage or transmission, the data may be transmitted or stored as a one dimensional sequence. It is to be recognized, that in certain embodiments, and as briefly described above, the X-ray emitter 42 and the X-ray receiver 44 are held in correspondence to one another and rotated about the object to be imaged P, exemplarily about a rotation axis. In an embodiment, the rotation axis is aligned with the center of the object to be imaged P. In the embodiment depicted in FIG. 2, the rotation axis is aligned with a particular anatomical feature of interest 50 within the patient's head P. In still further embodiments, the rotation axis may be variable, and in one example may move along a circular or other path. Other techniques or alignments for the rotation axis may also be used as will be recognized by a person of ordinary skill in the art.

The processor 48 receives the projection image data from the X-ray receiver 44 and the processor executes computer readable code that is stored on a computer readable medium 52. The execution of the computer readable code by the processor 48 causes the processor to perform data processing and control functions as disclosed in further detail herein, including to execute embodiments of methods of X-ray imaging, as disclosed in further detail herein. In a non-limiting example of processing and functionality carried out by the processor 48, the processor 48 reconstructs a 3D image from received projection images. A reconstruction as used herein is the application of an image processing algorithm that generates 3D data from projection images, modified projection images and/or other additional data as described in greater detail herein. The processor 48 is further connected to a graphical display 54. The processor 48 may operate the display 54 in such a manner as to present X-ray imaging data, which in embodiments, can be 2-D or 3-D X-ray images. In an exemplary embodiment, as referenced above, the display 54 may also include touch sensitive controls. For example, the display 54 can also operates as a user input device for a clinician or technician to enter control parameters or commands. While not depicted, in an additional embodiment, a separate user input device may also be used for such purposes. The processor 48 is communicatively connected to the X-ray emitter 42 to provide operation and control signals to the X-ray emitter 42, including, but not limited to controls regarding the timing and strength of the emitted beam 46 of X-rays.

Although the embodiment of the X-ray imaging system 40 depicted in FIG. 2 depicts a single processor 48, it will be recognized that in alternative embodiments, two or more processors may be used in coordination to function together to carry out the functions and operations as described herein. Therefore, references to the processor as found herein should be interpreted to include such multiple-processor systems.

The X-ray imaging system 40 further includes a filter 56. The filter 56 includes at least one filter leaf 58. In the exemplary embodiment depicted in FIG. 2, the filter 56 optionally, but not necessarily, includes a plurality of filter leaves 58. Each filter leaf 58 is constructed of an X-ray absorbent material, exemplarily lead, aluminum, copper, or tungsten. In embodiments, the at least one filter leaf 58 is adjustable in position to at least partially extend into the beam 46. The portions of the beam 46 that pass through one or more filter leaves 58 will be attenuated by the material of the filter leaf 58. Thus, the filter 56 modifies the beam 46 such that, for example the beam 46 includes (1) a limited field of view beam portion 60 where the X-rays reaches the object to be imaged P unattenuated by any of the filter leaves 58 of the filter 56, and (2) at least one attenuated beam portion 62 where the object to be imaged P is exposed to reduced X-ray intensity. Thus, the full field of view 64 of the beam 46 includes both the limited field of view beam portion 60 and the at least one attenuated beam portion 62. In the embodiment shown, the full field of view 64 includes the limited field of view beam portion 60 and two attenuated beam portions 62. While the embodiment shown depicts portions of the beam 46 being attenuated in a generally horizontal dimension, other embodiments may attenuate the beam 46 in a vertical dimension, or in both dimensions.

While not depicted, in FIG. 2, exemplary embodiments may also comprise a collimator positioned between the X-ray emitter 42 and the filter 56. The collimator blocks portions of the X-rays emitted from the X-ray emitter 42 to shape the emitted X-rays into beam 46. It will be recognized that in an exemplary alternative embodiment, the filter 56 may also operate as a collimator in that a sufficient number of filter leaves 58 may impinge on the beam 46 for example to block portions of the beam 46 entirely, In accordance with non-limiting and merely exemplary embodiments, the diameter of the full field of view may be between 30 millimeters and 180 millimeters. In certain embodiments, it is preferred that the full field of view is greater than a maximum diameter of the object or object portion to be imaged P—thus, for example as projection images from various angles about the object or object portion to be imaged P are obtained, such projection images capture the full size of the entire object or object portion to be imaged P. In non-limiting embodiments, the limited field of view can have a diameter of 30 millimeters-130 millimeters which can present a significantly reduced field of view to focus in on a specific anatomical structure of interest. Similarly, in embodiments, it is preferred that the diameter of the limited field of view be at least as large as, or slightly larger than, the maximum diameter of the anatomical structure of interest—thus, for example the entire anatomical structure of interest is captured within the limited field of view projection images.

In embodiments, the processor 48 provides control signals to the filter 56 to operate the filter 56—e.g., to adjust the position of one or more collimator leaves 58 either to adjust the size of the limited field of view beam portion 60 or to adjust an amount of attenuation of the X-rays in the attenuated portions 62 of the beam 46$m$ or both. In an embodiment, a plurality of filter leaves 58 are provided, each leaf 58 having an known X-ray absorption characteristic. Optionally, the filter can have one filter leaf 58 for each side of beam 46, or even just a single filter leaf 58. The known X-ray absorption characteristic of each filter leaf 58 can depend upon physical characteristics of the filter leaf. Two non-limiting examples of characteristics of the filter leaf include material or thickness. In an exemplary embodiment, the filter leaf may have one or more holes or perforations that reduce the X-ray absorption characteristic compared to filter leaves of solid construction. In an exemplary embodiment, the filter leaves each have the same X-ray absorption characteristic while in other exemplary embodiments the leaves each have different X-ray absorption characteristics.

The filter 56 can be operated to position an appropriate number of filter leaves 58 extending into the X-ray beam 46 to achieve a target attenuation based upon the strength of the X-ray beam projected from the X-ray emitter 42. In embodiments, the imaging system may perform a calibration procedure to map the actual attenuation of the X-rays by the at least on filter leaf 58. Natural variation in the emitted X-ray power or intensity, as well as natural variation, impurities, and manufacturing tolerances in the filter leaves 58, can result in some variance in the actual X-ray intensity in the attenuated portions. Therefore, a mapping or calibration, described in further detail below with respect to FIG. 3, can provide a more accurate representation of the X-ray intensity than default assumptions.

In clinical imaging, it is desirable to limit the X-ray dosage to which the patient is exposed, while using sufficient X-ray intensity to achieve a high quality medical image. One previous way in which this had been achieved is that when the specific anatomical structure of interest 50 is smaller than the entire object being imaged P, exemplarily the patient's head, a conventional collimator may be used to restrict the field of view of the X-ray bean) to only the size necessary to image the anatomical structure of interest. However, this has been found by the inventor to create problems in 3-D image reconstruction in that insufficient information regarding the anatomical structures around the anatomical structure of interest 50 is provided, which results in lower quality 3-D image reconstruction and a higher incidence of artifacts in the reconstructed 3-D images. Therefore, the system and method as disclosed herein provide for additional contextual information around the specific anatomical structure(s) of interest 50, while limiting the X-ray dose applied to the patient. In embodiments, new image processing techniques as disclosed herein are combined with the controlled adjustment of the filter leaves 58 in the filter 56 in order to attenuate, but not completely block, the portion of the X-ray beam 46 outside of the limited field of view beam portion 60. The projection images produced by this attenuated X-ray dose provide the context to make appropriate adjustments to improve 3-D image reconstruction of projection images from the limited field of view beam portion 60, which has been narrowed to specifically target the anatomical structures of interest.

In some cases, artifact-causing objects may still appear in the attenuated portion, but these can still be identified and the ROI compensated to remove any residual artifact. For example, artifact-causing objects, including but not limited to dental implants, are identifiable in the projection images outside of the limited field of view despite the attenuated X-ray dose. The identification of these artifact-causing objects can be used to improve image quality or remove the effects of these artifact-causing objects from the 3-D image reconstruction of the projection images from the limited field of view. In a non-limiting example, the projection images from outside of the limited field of view are normalized with the projection images from the limited field of view. From this normalized image a full field of view reconstruction can be performed. Within the full field of view reconstruction, the object of interest (e.g. the head of the patient) can be defined even though some or all of the edges of the object of interest are not located within the limited field of view, but rather are located in the attenuated portions outside of the limited field of view. In one non-limiting example this may be performed by separating the reconstructed image into air and non-air (e.g. the object) portions as these air/non-air edges are still readily identifiable within the attenuated portion. Thus, from the reconstructed full field of view image, embodiments are able to identify the shape and/or size of the object and locate the position of the limited field of view relative to the entire object of interest. This information, as well as other information as described in further detail herein can be used, for example, to improve the quality of the reconstructed volume. In still further exemplary embodiments, the quality of the reconstructed volume can be improved by calibrating the reconstruction with a known attenuation of the object of interest.

Limited field of view reconstructions may he susceptible to a non-uniform density distribution and may also be susceptible to increased density values caused by a high density mass located outside of the limited field of view. In an example of the non-uniform density distribution, an eccentric field of view projection image acquisition and the corresponding reconstruction from a head sized object, with uniform density, results in a reconstruction image with non-uniform density. The artifact in this example is the non-uniform density distribution. The non-uniformity is caused by a reconstruction from projection images in which it is indeterminate if a high density mass which appears in the projection images is inside or outside of the limited field of view. Similarly, when the high density mass is located outside of the limited field of view, this causes erroneously increased density values within the limited field of view reconstruction. If the mass outside of the limited field of view is located mainly in a specific direction from the field of view, then the density values in the limited field of view in that direction are increased more than the density values in other parts of the limited field of view. If the limited field of view is located, centrally to the mass, then while this may result in minimal non-uniformity artifacts as described above, the absolute density values of the entire limited field of view are shifted upward (e.g. by an unknown amount). Therefore, by locating the limited field of view, and the reconstruction from the limited field of view, within the object of interest, determinations can be made regarding the location of masses of increased density located within or outside the limited field of view and the reconstruction of the limited field of view thus improved as described in further detail herein.

Figure 3:
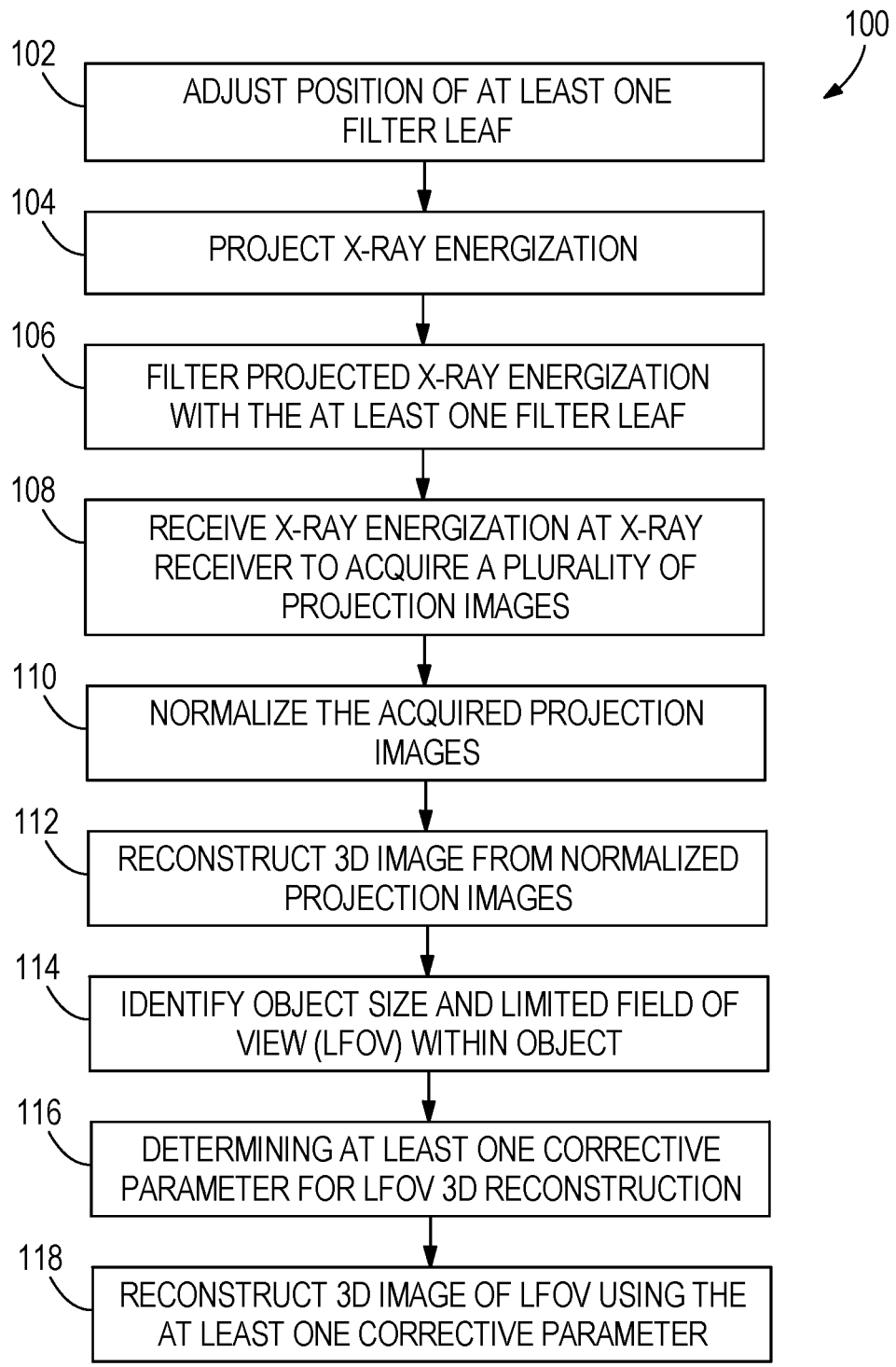
FIG. 3 is a flow chart that depicts an exemplary embodiment of a method of X-ray imaging.

FIG. 3 is a flow chart that depicts an exemplary embodiment of a method of X-ray imaging 100 in accordance with the invention. It is to be noted that the method 100 is presented merely as an example, and other embodiments may include more or fewer steps than those depicted in the method 100, or may perform such steps in an alternative order while achieving the same or similar functions as disclosed herein. At 102 the position of at least one filter leaf is adjusted in order to define one or both of the limited field of view diameter of the unattenuated portion of the X-ray beam and the attenuation of the X-rays in the attenuated portion of the X-ray beam. In some embodiments, the filter adjustment includes consideration of the desired X-ray intensity, which may be selected based upon the object to be imaged, and thus may require more or fewer filter leaves to achieve the appropriate attenuation.

Next at 104, X-rays are projected from an X-ray emitter in the direction of the X-ray receiver. The object to be imaged P, exemplarily the head of a patient, is disposed in the path of the projected X-rays between the X-ray emitter and the X-ray receiver. The X-rays can be projected in any of a variety of beam shapes, including, but not limited to, a fan, a line, or a cone, although it will be understood that other beam shapes may also be used. In the exemplary embodiment described herein, the X-ray beam is of a cone shape. In an embodiment wherein the X-rays are projected in a cone-shaped beam, the dimensions of the beam and the X-ray receiver can be selected to be larger than a maximum diameter of the object to be imaged P, thus fully capturing the object to be imaged P within the beam. The X-ray imaging system can control a power or intensity of the X-ray beam, which can be increased or reduced depending upon the specific object to be imaged P or the anatomical structures of interest within the object to be imaged P.

At 106 the projected X-rays are filtered by a filter that includes at least one filter leaf and is disposed at a position between the X-ray emitter and the object to be imaged as positioned at 102. The at least one filter leaf, which can be, for example, a plurality of filter leaves, partially extends into the X-ray beam and attenuates those portions of the beam to define (1) a limited, field of view where the X-ray beam is at full intensity, and (2) at least one attenuated portion wherein the X-ray beam has been partially absorbed by the at least one filter leaf. Thus, the collimator is operable to (1) define a limited field of view focused upon the anatomical structure of interest within the object to be imaged P, and (2) reduce the intensity of the X-rays outside of the limited field of view. As disclosed above, in some embodiments, the X-ray beam is collimated with a collimator before being filtered by the filter. In still further exemplary embodiments, the filter may also operate as a collimator if sufficient filter leaves impinge on the X-ray beam for example to absorb portions of the X-ray beam entirely.

The X-ray beam, which now has both a limited field of view beam portion of full intensity X-rays and at least one attenuated beam portion, passes through the object to be imaged P and is received at 108 by an X-ray receiver to acquire a projection image. In general, there is a relationship between the X-ray intensity and the signal to noise ratio ("SNR") of the acquired image, up to the saturation point of the sensor. Therefore, the anatomical structures of interest imaged with the limited field of view with a full intensity of X-rays will generally have a higher SNR in the projection image, while the portions of the object to be imaged that receive the attenuated X-rays will have a lower SNR. It will be understood that in embodiments as disclosed herein a plurality of projection images are acquired by incrementally rotating the X-ray emitter and the X-ray receiver about the object to be imaged and repeating steps 104, 106, and 108 in order to acquire projection images taken from a plurality of angles about the object to be imaged P.

As noted above, the portions of the object to be imaged P that receive the full intensity X-rays will have both higher intensity measurements and a higher SNR than those portions of the object to be imaged that received attenuated X-rays. Therefore, at 110 the acquired projection images are normalized to adjust for differences in the image quality and image intensity between these portions of the projection images. In one embodiment, the normalization is performed based upon test images that are captured at a calibration phase for the system. The test images taken during the calibration of the system provide information about the intensity and distribution of the X-rays after attenuation by the collimator, and about the impact of the attenuation on the individual pixel values of the projection images. Thus, the normalization at 110 can normalize the individual pixel values of the projection images based upon the attenuation mapped during the system calibration. The result is a set of 2D projections, each containing not only the particular anatomical feature of interest 50, but as the region surrounding the feature of interest 50, optionally (but not necessarily) including the entire object P. Each projection can, for example, be processed by the 3D reconstruction algorithm (as described below) in the same manner as if the entire projection was created with a uniform X-ray dose. The normalized portions of each projection representing the region outside the feature of interest 50 will tend to be noisier (i.e., have lower SNR) due to the reduced dose in those regions, but their quality is sufficient to reduce truncation artifacts, object-based artifacts, ad other artifacts that might otherwise appear in the 3D reconstruction of the feature of interest 50, while the high-SNR portions of the projections allow for a high-SNE 3D reconstruction of the feature of interest.

At 112 a 3-D image is reconstructed from the normalized projection images. In this 3-D reconstruction, the object to be imaged P is reconstructed using the projection image data acquired in both the limited field of view and the attenuated portions of the X-ray beam. The 3-D image reconstruction can be performed using a variety of techniques and algorithms as may be recognized by a person of ordinary skill in the art.

At 114 the size of the object to be imaged P is identified. Since the anatomical structure of interest is typically located internally to the object to be imaged P, the exterior sides or edges of the object to be imaged P will be imaged by the attenuated portions of the X-ray beam. While the attenuated X-rays limits the detail and/or quality of the reconstructions of these portions of the object to he imaged P, even at this reduced image quality, the exterior edges of the object to be imaged P can be determined due to the inherent contrast between object and air in the projection images. Once the object size and edges are identified, the limited field of view around the anatomical structure of interest can be identified and located within the larger defined image object. In non-limiting embodiments, the field of view about the object to be imaged is between 30 millimeters and 180 millimeters while the limited field of view diameter is between 30 millimeters and 130 millimeters wherein the limited field of view is smaller than the full field of view.

Alternatively, or in addition, one or more artifact-causing objects may be identified in the 3-D reconstruction outside of the limited field of view. The identification of the artifact-causing objects can be used as disclosed herein to improve the quality of the reconstruction of the limited field of view. As described above, these objects may be higher density objects that produce artifacts in the density distribution of the limited field of view reconstruction. In an embodiment wherein the artifact-causing object is a mass is located outside of the limited field of view, identification of the mass can be used to estimate the erroneous increase in density of the limited field of view reconstruction.

Once the limited field of view is identified within the larger defined object to be imaged P, this additional information regarding position of the limited field of view within the imaged object is used at 116 to define at least one corrective parameter for use in the 3-D reconstruction of the projection images from the limited field of view. The at least one corrective parameter can include, for example, the local mass distribution in the anatomical structures outside of the limited field of view and/or positional information related to the relative positions and size of the limited field of view within the imaged object. The at least one corrective parameter can be a function or value that is able to eliminate the non-uniform distributions of density from the limited field of view reconstructed image by supplementing the incomplete information with deduced extrapolated and/or generalized information of the full objects. In an embodiment, the corrective parameter may be a linear function, exemplarily a function of a 3D plane. Such corrective parameter is applied to or replaces the density distribution to improve overall density distribution in the reconstructed image. Corrective parameters may in other embodiments be produced empirically, by simulation, or analytically.

Embodiments as disclosed herein deduce information about an object's full size (e.g. in horizontal dimensions) when that object extends outside of the limited field of view. As non-limiting examples, embodiments achieve this additional information by: 1) a two reconstruction solution whereby the object's full size is deduced from a first reconstructed volume image, and 2) an object's full size is deduced directly from projection images using known projection image of position geometry.

In the two reconstruction embodiment, before a first reconstruction, the projection images are segmented into modified projection images of two components: an air component (no attenuation) and an object component (e.g. the rest of the projection image data). Next, modified projection images are created from the segmented projection images. The modified projection images constitute image data only from one of the air components and the object component in an embodiment, the object component is further represented with a homogenous attenuation. The full object (e.g. head) size information is deduced from reconstructions of the modified projection images. In the second reconstruction, the full object size information is used to supplement the incomplete information available from the limited field of view projection images.

In the embodiment wherein the full object's size is deduced directly form the projection images, often an object's outer edge (e.g. the skin-air boundary) is visible somewhere near an edge of the projection images. From the projection images, even in the attenuated portion of the projection images, the skin-air-edge may be identified. By identifying the skin-air boundaries, this embodiment directly determines an amount of the object that exists out of the limited field of view.

Once the object full size information is deduced, exemplarily in one of the two embodiments as discussed above, this information can be used to improve the reconstruction of images, e.g. human medical and 3D dental applications. These reconstructions may be unproved by further assuming, that the head average density is roughly the same as with water. The density of the portions of the object outside of the limited field of view can be assumed to be the density of water or another density as predetermined in an application or selected by a user. At least one corrective parameter, as mentioned above, can be applied to the projection images, exemplarily to the projection image intensities that represent the object attenuation.

In an ideal condition, without the truncation of the projection image to the limited field of view projection images, the total attenuation represented in the projection image is independent from the scan angle. This ideal condition is only true if the whole object is fully visible in all of the projection images. When the limited field of view projection images are used, the ideal condition can be approximated by adding the missing parts of the full object at a generalized density to the projection images by extrapolation if the full object size has been determined, exemplarily m one of the manners as explained above. By extrapolating the projection images in the approximated missing parts of the projection images to the total attenuation of projection images of the full object can be normalized to thus be the same between projection images and independent from projection angle. In an embodiment, the extrapolated attenuation is redistributed within each projection image by keeping the total attenuation per scan angle constant. Redistribution of the values from the portions of the object outside of the limited field of view can be uneven and approximate the original full object as much as possible. In a non-limiting embodiment, if there is only truncation of a left side of an imaged object then the redistribution will be mainly shared to the left side of the limited field of view projection images.

Limited field of view projection images contain some detail from outside the limited field of view volume because each projection image is a two-dimensional representation of X-rays passing, through a three dimensional section of the object being imaged. In addition, the defined at least one corrective parameter can contain information regarding the location of the anatomical structure of interest within the imaged object. This provides context for the 3-D reconstruction of the limited field, of view projection images, which helps to identify that image information from outside the limited field of view volume found within the limited field of view projection images. As described above, by locating the anatomical structure of interest within the imaged object, information regarding the location of increased density masses is obtained. By determining whether these masses are within or outside of the limited field of view reconstruction, non-uniform density distribution or erroneously increased density value artifacts may be identified and corrected. For example, by identifying a location of an increased density mass outside of the limited field of view, the total density distribution of the full object can more accurately be known and the density distribution within the limited field of view projection image corrected to be reflective of this information. In a further embodiment, the at least one corrective parameter is based upon an artifact-causing object in the reconstruction. The corrective parameter can be used to reduce or eliminate the effects of this artifact-causing object found in the reconstruction of the limited field of view. For example, as described above, an identified non-uniform density distribution can be corrected by flattening the density distribution in the reconstruction with a density value or function applied across the projection images. Additionally, if based upon the location of a mass outside of the limited field of view, the reconstruction has an erroneously increased density distribution, the density distribution within the limited field of view can be corrected downwards to maintain the density distribution of the whole object.

The at least one corrective parameter is used at 118 to reconstruct a 3-D image of the limited field of view portions of the projection images acquired using the full intensity portion of the X-ray beam resulting in a higher signal quality. As described above, a non-uniform density distribution can be corrected with the corrective parameter to flatten the density distribution in the limited field of view reconstruction. The limited field of view reconstruction may also be susceptible to inaccurate determination of density values, which may also be considered to be a form of artifact. In a non-limiting example, a doctor or clinician may be unable to determine a true density of at least one tissue from the reconstruction (e.g., whether a bone is hard or soft or to determine an amount of error between the reconstructed density and the actual density). In an exemplary embodiment, the corrective parameters may be used to simulate the expected density. For example, a simulation of the whole object to be imaged and density distribution of the whole object can yield an estimate of an expected density of a particular anatomical object, or an expected density distribution across the whole object. A density value from this simulation may be used to decrease the error in the reconstructed density value. In embodiments, the development of the at least one corrective parameter may include the use of presumptions of object density and density distribution within the limited field of view. As the presumptions become more sophisticated and detailed, the resulting corrective parameters may further improve limited field of view reconstruction. The reconstructed 3-D image of the limited field of view portion of the projection image can be presented on a graphical display or stored on a computer readable medium for later access by a user.

Embodiments of the system and/or method disclosed herein may be used in connection with an X-ray imaging device that is capable of providing normal full field of view imaging or limited field of view imaging. Exemplarily, full field of view imaging may be performed by adjusting the at least one collimator leaf to be outside the X-ray beam for example no portion of the X-ray beam is attenuated. Similarly, standard limited field of view imaging may be performed by using a plurality of collimator leaves for example most or all of the X-rays in the attenuated portions of the X-ray beam is absorbed by the combined collimator leaves and thus only the limited field of view portion of the X-ray beam passes through the object to be imaged and is imaged.

It has been discovered that in the desire to limit X-ray dosage in patients, the reduction of the field of view diameter can eliminate important contextual information used to provide a high quality 3-D reconstruction. Therefore, the presently disclosed system and method provides a solution whereby the X-ray dose can be limited by the use of a small diameter limited field of view projection for the 3-D reconstruction that can be tightly adjusted to the dimensions of the anatomical structure to be imaged while attenuated X-rays are exemplarily applied to the surrounding area or peripheral area of the object to be imaged in order to acquire the contextual information used to achieve a high quality 3-D reconstruction of the limited field of view projection images.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. An X-ray imaging system, the system comprising:
   an X-ray emitter configured to produce a first X-ray beam;
   a filter disposed to receive the first X-ray beam and output a second X-ray beam comprising a higher-intensity beam portion and a lower-intensity beam portion, the filter comprising at least one filter leaf adapted to attenuate a portion of the first X-ray beam to produce the lower-intensity beam portion, the at least one filter leaf being adjustable to adjust at least one of an intensity of the lower-intensity beam portion and a geometry of the lower-intensity beam portion, the X-ray emitter and filter being arranged to direct the second X-ray beam toward an object;
   an X-ray receiver positioned to receive unabsorbed X-rays from the second X-ray beam, wherein the filter is disposed between the X-ray emitter and the X-ray receiver, the X-ray receiver configured to produce a plurality of projection images of the object from the received unabsorbed X-rays, each of the plurality of projection images comprising a first region generated from the lower-intensity beam portion and a second region generated from the higher-intensity beam portion; and
   a processor in communication with the X-ray receiver, the processor adapted to execute computer readable code stored upon a computer readable medium, and upon execution of the computer readable code, to perform the steps of:
      receiving the plurality of projection images from the X-ray receiver;
      determining at least one corrective parameter based upon the plurality of projection images; and
      reconstructing a first three dimensional image using the at least one corrective parameter and the second regions of the plurality of projection images.

2. The X-ray imaging system of claim 1, wherein determining at least one corrective parameter from the plurality of projection images further comprises:
   producing a reconstruction based upon the plurality of projection images wherein the at least one corrective parameter is determined from the reconstruction.

3. The X-ray imaging system of claim 2, wherein producing the reconstruction comprises normalizing at least one of the first and second regions of each projection image in the plurality of projection images, wherein the reconstruction is produced from the normalized projection images.

4. The X-ray imaging system of claim 1, wherein the X-ray emitter is a cone beam X-ray emitter.

5. The X-ray imaging system of claim 4, wherein the at least one filter leaf is adjustable in position to define the geometry of the lower-intensity beam portion.

6. The X-ray imaging system of claim 1, wherein the filter is configured to pass substantially unattenuated X-rays from the X-ray emitter to produce the higher-intensity beam portion and to direct the higher-intensity beam portion to a selected portion of the object, and wherein the filter is further configured to direct the lower-intensity beam portion to a portion of the object located outside the selected portion of the object.

7. The X-ray imaging system of claim 1, wherein the at least one filter leaf comprises a plurality of filter leaves, each filter leaf of the plurality being configured to absorb a predetermined portion of X-rays, wherein the plurality of filter leaves are adjustable within the filter to define the geometry of the higher-intensity beam portion, and to define an attenuation of the X-rays in the lower-intensity beam portion.

8. The X-ray imaging system of claim 1, further comprising a graphical display operable by the processor to present the reconstructed three dimensional image based upon the selected portion of the object.

9. A method of X-ray imaging, comprising:
   projecting a first X-ray beam from an X-ray emitter;
   filtering the first X-ray beam with a filter to produce a second X-ray beam comprising a higher-intensity beam portion and a lower-intensity beam portion, the filter comprising at least one filter leaf that absorbs at least a portion of the projected X-rays to produce the lower-intensity beam portion;
   receiving X-rays from the second X-ray beam at an X-ray receiver to acquire a plurality of projection images, each of the plurality of projection images comprising a first region generated from the lower-intensity beam portion and a second region generated from the higher-intensity beam portion;
   determining at least one corrective parameter based upon the plurality of projection images; and
   reconstructing, with a processor, a three dimensional image using the at least one corrective parameter and the second regions of projection images.

10. The method of claim 9, wherein determining at least one corrective parameter from the plurality of projection images comprises:
    producing a reconstruction from the plurality of projection images and determining the at least one corrective parameter from the reconstruction.

11. The method of claim 10, wherein determining at least one corrective parameter form the plurality of projection images further comprises:
    normalizing at least one of the first and second regions of each projection image in the plurality of projection images;
    wherein the reconstruction is produced from the normalized projections images.

12. The method of claim 10, further comprising presenting the reconstructed three dimensional image on a graphical display.

13. The method of claim 9, further comprising locating a limited field of view within the plurality of projection images by identifying a size of an object to be imaged and a position of the limited field of view within the plurality of projection images.

14. The method of claim 9, wherein the at least one corrective parameter is based upon the identified size of the imaged object and the identified position of the limited field of view in the reconstructed first three dimensional image.

15. The method of claim 9, wherein the at least one filter leaf comprises a plurality of filter leaves, the method further comprising adjusting relative positions of the plurality of filter leaves to thereby control the attenuation of the X-rays in the lower-intensity beam portion.

16. The method of claim 15, further comprising adjusting the relative positions of the plurality of filter leaves to define the geometry of the higher-intensity beam portion.

17. The method of claim 15, further comprising adjusting the relative positions of a plurality of filter leaves to collimate the x-rays projected from the X-ray emitter by blocking entirely a portion of the X-rays projected from the X-ray emitter.

* * * * *